United States Patent [19]

Le Goff et al.

[11] 4,209,424

[45] Jun. 24, 1980

[54] CATALYST FOR MANUFACTURING AMINES FROM ALCOHOLS

[75] Inventors: Yannick Le Goff, Saint Nazaire; Michel Senes, La Baule; Christian Hamon, Saint Nazaire, all of France

[73] Assignee: Societe Chimique de la Grande Paroisse, Azote et Products Chimiques, Paris, France

[21] Appl. No.: 966,736

[22] Filed: Dec. 5, 1978

Related U.S. Application Data

[63] Continuation-in-part of Ser. No. 904,285, May 9, 1978, abandoned.

[30] Foreign Application Priority Data

Dec. 12, 1977 [FR] France ............................... 77 37346
Jul. 4, 1978 [FR] France ............................... 78 19875

[51] Int. Cl.² .................. B01J 21/04; B01J 23/72; B01J 23/74; B01J 23/46
[52] U.S. Cl. .................. 252/474; 252/454; 252/459; 252/462; 252/463; 252/466 J; 252/472; 252/476; 260/585 B
[58] Field of Search ............ 252/466 J, 466 B, 472, 252/454, 459, 462, 474, 476, 463; 260/585 B

[56] References Cited

U.S. PATENT DOCUMENTS

| 3,270,059 | 8/1966 | Winderl et al. | 260/585 B |
| 3,520,933 | 7/1970 | Adam et al. | 252/470 X |
| 3,814,684 | 6/1974 | Christman et al. | 208/216 PP |
| 4,134,856 | 1/1979 | Itoh et al. | 252/465 X |

FOREIGN PATENT DOCUMENTS

| 2310802 | 5/1976 | France . | |
| 2325427 | 8/1976 | France . | |
| 2337585 | 1/1977 | France . | |
| 1206659 | 9/1970 | United Kingdom | 260/585 B |

*Primary Examiner*—W. J. Shine
*Attorney, Agent, or Firm*—Browdy and Neimark

[57] ABSTRACT

A catalyst for implementing a process for manufacturing amines from alcohols is composed of an active element in the transition metals family uniformly combined with a refractory porous structure with a specific surface of between 10 and 300 m²/g and with a pore diameter less than 5000 Å. A stabilizer in the form of a sodium-based compound with a sodium content of 0.15 to 20% by weight relative to the weight of the catalyst, and a promoter in the form of a rhodium-based compound with a maximum rhodium content of 0.1% by weight relative to the weight of the catalyst, may be associated with the active metal. The catalyst and the process are applicable to the ethanolamine-ammonia reaction with a view to producing ethylenediamine, piperazine, and useful byproducts.

10 Claims, No Drawings

CATALYST FOR MANUFACTURING AMINES FROM ALCOHOLS

CROSS-REFERENCE TO RELATED APPLICATION

The present application is a continuation-in-part of copending U.S. application Ser. No. 904,285, filed May 9, 1978, now abandoned the entire contents of which are hereby incorporated by reference.

FIELD OF THE INVENTION

The present invention relates to a catalyst for working a process for manufacturing amines from alcohols, in particular ethanolamines.

BACKGROUND OF THE INVENTION

There are essentially two methods for manufacturing ethylenediamine industrially. Most of the production capacity is based on dichloroethane; however, this process produces sodium chloride contaminated with amines, making it difficult to recycle. Thus the manufacture of amines from ethanolamine is an attractive method provided that the ethanolamine-ammonia reaction is conducted in the presence of an effective, selective, and long-lived catalyst.

Catalysts based on magnesium oxide have been proposed, but they have been found to deteriorate when they come into contact with the reaction medium; hydration of the magnesium substrate causes a loss of mechanical strength and a rapid decline in activity.

SUMMARY OF THE INVENTION

According to the present invention, an amination catalyst has been found, catalyzing in particular the ethanolamine-ammonia reaction with a view to production of ethylenediamine, piperazine, and useful by-products such as diethylenetriamine, aminoethylpiperazine, aminoethylethanolamine, and hydroxyethylpiperazine. This catalyst has excellent mechanical strength which is retained, plus a greater lifetime than that of known catalysts with this application. The activity of the catalyst after an operating period of six months is very similar, and in particular the ethylenediamine yield does not change, by comparison with the initial results. As a function of the catalyst and various process parameters, the reaction can be oriented selectively with respect to ethylenediamine, piperazine, or the heavier amines, so that manufacture can be adjusted to market requirements. The catalyst can advantageously be used in various hydrogenation reactions.

The amination catalyst is composed of an active element in the transition metals family and is uniformly allied to a refractory porous structure with a specific surface between 10 and 300 m$^2$/g and with a pore diameter less than 5,000 Å.

According to a preferred embodiment of the present invention, catalysts have been found with an even longer lifetime. The improvement is very substantial from the standpoint of the mechanical strength of the assembly and preservation of reactivity. Even after a long period of activity, the ethylenediamine yield is not subject to variations relative to the initial results. The catalytic activity remains perfectly stable, and does not undergo any mechanical changes after more than 5000 hours of operation. The results of various continuous processes confirm these advantages.

In this preferred embodiment a stabilizer in the form of a sodium-based compound with a sodium content of 0.15 to 20% by weight of the catalyst, and a promoter in the form of a rhodium-based compound with a maximum rhodium content of 0.1% by weight relative to the weight of the catalyst, may be associated with the active metal.

DETAILED DESCRIPTION OF PREFERRED EMBODIMENTS

The preferred active metal is nickel, used alone or in association with other transition metals such as copper and cobalt; nickel represents at least 50% of the active substance. The transition metals content represents 30–70% of the total catalyst weight.

The microporous substrate is at least one oxide chosen from the group consisting of alumina, silica, thorium oxide, and cerium oxide.

In accordance with a preferred embodiment of the present invention, it has been discovered that the stability of the catalysts is improved by the presence of sodium. Advantageous results have been obtained by associating with the active metal, a sodium-based compound with a sodium content between 0.15 and 20% by weight of catalyst. In particular, a 5 to 10% sodium content has been selected for the stabilizing effect it produces.

It has further been noted that the activity of the catalyst is enhanced by the presence of a promoter. This promoter is preferably in the form of a rhodium-based compound with a maximum rhodium content of 0.1% by weight relative to the weight of the catalyst.

The specific surface of this preferred catalyst is between 10 and 300 m$^2$/g, preferably between 30 and 50 m$^2$/g. The pore diameter is less than 5000 Å.

The structure of the catalyst can be obtained by co-precipitation of all the catalyst elements from soluble salts by a base or carbonate, or from soluble salts in a basic medium by lowering the pH. The structure can also be constituted by impregnating the active elements on the previously combined refractory oxides with a soluble salt; the impregnation can advantageously be conducted in a vacuum. When sodium is present it is introduced, in the form of salts or combined with the refractory porous substrate, either during the precipitation and mixed in during the course of elimination by washing, or by impregnation on the catalyst at any stage in its manufacture.

It is advantageous for all the elements of the catalyst to be coprecipitated from soluble salts such as nitrates. The sodium may be introduced as sodium carbonate.

The precipitating agent, used in a stoichiometric quantity, is generally a base (ammonia, sodium hydroxide, or potassium) or a carbonate. The precipitate obtained constituted by a mixture of hydroxides is filtered then rinsed and dried at a temperature between 80° and 120° C.

All the elements can also be coprecipitated from soluble salts in a basic medium by lowering the pH. For example, for preparing a nickel catalyst on alumina or silica, the nickel is in the form of a $[Ni(NH_3)_4]^{++}$ complex obtained by adding a large excess of $NH_4OH$ to a solution of nickel nitrate, the aluminum being in the form of sodium aluminate and the silicone in the form of sodium silicate. As before, the precipitate obtained is filtered, rinsed, and dried at a temperature between 80° and 120° C.

When the structure is formed by coprecipitation, the transition metals can be adjusted to the desired level.

According to the impregnation version, the porous substrate composed of one or more of the aforementioned oxides is made separately. The substrate is then impregnated with a soluble salt of the active element, then dried at a temperature of 80° to 120° C. The soluble salt is generally a nitrate. It is advantageous to pretreat the substrate by drying or degassing, and impregnation is conducted in a vacuum. Hence, the amount of active substance deposited is increased. Impregnation can be carried out in several stages with intermediate drying for the same purpose.

The transition metal associated with the microporous substrate is subjected to direct reduction by scavenging with a reducing gas (such as an $N_2/H_2$ mixture) between 400° and 550° C. for several hours, about 8-10 hours, with a temperature rising from ambient temperature to the reduction temperature by 50° C. per hour. After reduction, the transition element is in the metal form and uniformly distributed on the substrate.

The catalyst can advantageously be subjected to prior decomposition by heat treatment in air at a temperature between 350° and 500° C. for several hours, with a gradual rise from ambient temperature to the decomposition temperature of 50° C. per hour.

The amination catalyst according to the present invention is advantageously applicable to a catalytic process in a heterogeneous phase for producing ethylenediamine and piperazine from ethanolamine and ammonia. It makes no difference whether this process is carried out discontinuously or continuously, namely in a closed reactor with agitation or in an open reactor with continuous circulation of the reaction mixture over the catalyst.

The ethanolamine ammonia reaction in the presence of the amination catalyst is conducted at a temperature between 170° and 260° C. at a pressure between 50 and 300 bars absolute. The ethanolamine, ammonia, and hydrogen are introduced into the reactor in quantities such that the ammonia/ethanolamine molar ratio is between 5 and 40 and the hydrogen flow rate is between 5 and 200 Nl per mole of ethanolamine.

The reaction may be carried out in the presence of water, the latter being introduced into the reaction mixture until its weight is 25% of that of the ethanolamine.

It is advantageous to recycle the reactants which have not reacted or those in excess such as unconverted ethanolamine and excess ammonia. Partial or total recycling of one of the products piperazine with ethanolamine, can also be an attractive possibility.

Examples of preparing catalysts and applying the process in the presence of these catalysts, possibly with recycling, are given hereinbelow.

In the following examples, the term "heavy product" designates all of the following compounds: diethylenetriamine, aminoethylpiperazine, aminoethylethanolamine and hydroxyethylpiperazine. The abbreviations E.D.A., PIP, and E.A. designate ethylenediamine, piperazine, and ethanolamine respectively.

EXAMPLE 1

Catalyst 1: (Nickel on alumina). 459.7 g of crystallized aluminum nitrate [$Al(NO_3)_3.9H_2O$] dissolved in 1350 cc of water are added to 286.5 cc of a nickel nitrate solution with density 1.53 and containing 14.26% by weight of nickel. This solution is added while stirring to 2.3 l of a solution containing 232.5 g of soda. The suspension obtained is boiled for 10 minutes. After cooling, it is filtered through a Buchner funnel and rinsed with 2 l of water at 20° C. to eliminate the sodium nitrate. The precipitate is then dried at 100° C. then formed into cylindrical pellets (5×5 mm). These pellets are then decomposed in air at 400° C., the temperature being raised gradually at the rate of 50° C. per hour and the top level of 400° C. being held for six hours. The catalyst thus obtained is then reduced in a mixture of reducing gas ($N_2+3H_2$) at 450° C. for 8 hours; the temperature rise is 50° C. per hour. The nickel content of the catalyst is 50% and its specific surface is 116 m²/g.

Application: 50 g of ethanolamine, 140 g of ammonia, 7.46 g of catalyst 1, and 11.8 Nl of hydrogen are placed in a 550 cc autoclave fitted with a stirrer. The $NH_3E.A.$ molar ratio is 10, and the quantity of hydrogen is 14.4 Nl/mole of E.A. The mixture is stirred for 8 hours at a temperature of 205° C. and a pressure of 198 bars absolute. The reaction product is analyzed by gas chromatography and the results are shown in the tables below.

| % E.A. Converted | | Yield in weight %/Initial E.A. | | Wt. % Yield/E.A. Consumed | |
|---|---|---|---|---|---|
| into E.D.A. | 30.6 | of E.D.A. | 30.2 | of E.D.A. | 53.6 |
| into PIP | 15.2 | of PIP | 10.7 | of PIP | 19.0 |
| into heavy product | 10.5 | of heavy product | 8.0 | of heavy product | 14.2 |
| TOTAL | 56.3 | of $H_2O$ | 16.4 | | |
| | | of unconverted E.A. | 43.7 | | |
| | | TOTAL | 109.0 | | |

EXAMPLE 2

Catalyst 2: (Nickel on alumina). The following are dissolved in 2.8 l of water: 735.5 g of crystallized aluminum nitrate $Al(NO_3)_3.9 H_2O$ and 495.4 g of crystallized nickel nitrate Ni $(NO_3)_2.6 H_2O$. This solution is poured into 5 l of a potassium solution containing 521 g of KOH while stirring. The precipitate is filtered then rinsed with 6 l of demineralized water; it is dried for 12 hours at 90° C., then decomposed in air for 5 hours at 400° C., the temperature being raised at the rate of 50° C. per hour. After being formed into 5×5 mm pellets it is reduced in a mixture of $N_2$ and 3 $H_2$ (400 Nl/h), the temperature being raised from ambient temperature to 450° C. at the rate of 50° C. per hour and is held at 450° C. for 10 hours. The nickel content of the catalyst is 50% and the residual potassium content is 2.4%; its specific surface is 156 m²/g.

Application: 50 g ethanolamine, 140 g ammonia, 7.50 g catalyst 2 and 11.8 Nl of hydrogen are placed in the same autoclave as before. They are agitated for 8 hours at a temperature of 205° C. and a pressure of 204 bars absolute. The results are shown in the table below.

| % E.A. Converted | | Yield in weight %/Initial E.A. | | Wt. % Yield/E.A. Consumed | |
|---|---|---|---|---|---|
| into E.D.A. | 46.2 | of E.D.A. | 45.4 | of E.D.A. | 64.8 |
| into PIP | 14.8 | of PIP | 10.4 | of PIP | 14.9 |
| into heavy product | 9.2 | of heavy product | 7.4 | of heavy product | 10.5 |
| TOTAL | 70.2 | of $H_2O$ | 20.6 | | |
| | | of unconverted E.A. | 29.9 | | |

| % E.A. Converted | Yield in weight %/Initial E.A. | Wt. % Yield/E.A. Consumed |
|---|---|---|
| | TOTAL 113.7 | |

EXAMPLE 3

Catalyst 3: (Nickel on alumina). 260 cc of concentrated ammonia (13 moles per l) are added to a solution of 320 cc of nickel nitrate containing 49.5 g of crystallized nickel nitrate $Ni(NO_3)_2.6 H_2O$. The solution obtained is a clear blue, due to the formation with the ammonia of the soluble nickel tetramine complex. To this solution is added 28 cc of a sodium aluminate solution, density 1.52, containing 360 g/l $Al_2O_3$. The mixture is introduced into a 2 l flask and the ammonia is evaporated by entrainment with superheated steam until the medium is neutral. The precipitate obtained is then filtered, rinsed with 2 l of water, then dried at 80° C. After decomposition in air at 400° C. it is formed into cylindrical pellets (5×5 mm) then reduced for 8 hrs. at 450° C. in a reducing gas mixture ($N_2+3H_2$), the temperature rise for decomposition and reduction being 50° C. per hr. The nickel content of the catalyst is 50% and its specific surface is 131 m²/g.

Application: 50 g ethanolamine, 140 g ammonia, 10 g water, 8.58 g catalyst 3 and 11.8 Nl hydrogen are placed in the autoclave of example 1. They are stirred for 8 hrs. at a temperature of 195° C. under a pressure of 160 bars absolute. The results are set forth in the tables below.

| % E.A. Converted | | Yield in weight %/Initial E.A. | | Wt. % Yield/E.A. Consumed | |
|---|---|---|---|---|---|
| into E.D.A. | 31.4 | of E.D.A. | 30.9 | of E.D.A. | 54.7 |
| into PIP | 13.8 | of PIP | 9.7 | of PIP | 17.3 |
| into heavy product | 11.3 | of heavy product | 8.5 | of heavy product | 15.0 |
| TOTAL | 56.5 | of $H_2O$ | 36.2 | | |
| | | of unconverted E.A. | 43.5 | | |
| | | TOTAL | 128.8 | | |

EXAMPLE 4

Catalyst 4: (Nickel on alumina). The following are dissolved in 5 l of water: 1470 g of crystallized aluminum nitrate and 778 g of crystallized nickel nitrate. 5.5 l of a soda solution containing 685 g of NaOH are added with agitation. The precipitate is filtered and rinsed with 11 l of water; the precipitate is dried for 12 hrs. at 80° C. then decomposed in air at 250° C., the temperature being raised at the rate of 50° C. per hr. and the top temperature being held for 5 hrs.; it is then formed into 5×5 mm pellets. It is reduced at 450° C. for 8 hrs. in an $N_2+3H_2$ mixture, the temperature being raised gradually from ambient temperature at the rate of 50° C. per hr. The weight of the product obtained is 350 g. The nickel content of the catalyst is 44% and its specific surface is 164 m²/g.

Application: 50 g ethanolamine, 140 g of ammonia, 10 g of water, 7.26 g of catalyst 4, and 11.8 Nl of hydrogen are placed in the autoclave of example 1. They are stirred for 8 hrs. at a temperature of 195° C. and a pressure of 160 bars absolute. The results are shown in the tables below.

| % E.A. Converted | | Yield in weight %/Initial E.A. | | Wt. % Yield/E.A. Consumed | |
|---|---|---|---|---|---|
| into E.D.A. | 33.1 | of E.D.A. | 32.6 | of E.D.A. | 65.6 |
| into PIP | 5.0 | of PIP | 3.6 | of PIP | 7.1 |
| into heavy product | 11.7 | of heavy product | 8.7 | of heavy product | 17.6 |
| TOTAL | 49.8 | of $H_2O$ | 34.5 | | |
| | | of unconverted E.A. | 50.3 | | |
| | | TOTAL | 129.7 | | |

EXAMPLE 5

Catalyst 5: (Nickel on alumina). 576.6 g of crystallized nickel nitrate are dissolved in 1.25 l of water. 2.95 l of an ammonia solution (13.5 moles/l) are added and the mixture is stirred until all the nickel hydroxide has been dissolved; 450 cc of a solution of sodium aluminate containing 211.5 g of aluminate with 49.8 wt.% $Al_2O_3$ are added to this solution. The mixture is stirred and the excess ammonia driven off by heating at 70° C. until the vapors given off are neutral. The precipitate obtained is filtered and rinsed with 6 l of demineralized water. It is dried at 80° C. for 12 hrs., decomposed at 300° C. for 5 hrs., then reduced in an $N_2+3H_2$ (400 Nl/h) mixture at 450° C. for 8 hrs., the temperature rise for decomposition and reduction being 50° C. per hr. The nickel content of the catalyst is 52.5% and its specific surface is 124 m²/g.

Application: 50 g of ethanolamine, 140 g of ammonia, 10 g of water, 7.63 g of catalyst 5, and 11.8 Nl hydrogen are placed in the autoclave of example 1. They are agitated for 8 hrs. at a temperature of 195° C. and a pressure of 128 bars absolute. The results are set forth in the tables hereinbelow.

| % E.A. Converted | | Yield in weight %/Initial E.A. | | Wt. % Yield/E.A. Consumed | |
|---|---|---|---|---|---|
| into E.D.A. | 32.0 | of E.D.A. | 31.6 | of E.D.A. | 64.4 |
| into PIP | 9.3 | of PIP | 6.5 | of PIP | 13.3 |
| into heavy product | 7.8 | of heavy product | 6.0 | of heavy product | 12.3 |
| TOTAL | 49.1 | of $H_2O$ | 34.4 | | |
| | | of unconverted E.A. | 51.0 | | |
| | | TOTAL | 129.5 | | |

EXAMPLE 6

Catalyst 6: (Ni-Cu on alumina). The following are dissolved in 1.8 l of water: 441.3 g of crystallized aluminum nitrate, 267.5 g of crystallized nickel nitrate, and 22.8 g of crystallized copper nitrate. This solution is added, while stirring, to 1.6 l of soda solution containing 222 g of NaOH. The precipitate is rinsed with 4 l water at 20° C. then dried at 90° C. for 12 hrs. It is then ground (less than 0.5% remaining in a 200 μ mesh) then mixed with 1% graphite and formed into cylindrical pellets (5×5 mm). It is then reduced in an $N_2+3H_2$ mixture (300 Nl/h) at 450° C. for 8 hrs., the temperature rising from ambient temperature at the rate of 50° C. per hr. The nickel content of the catalyst is 45%, the copper content 5%, and its specific surface 136 m²/g.

Application: 50 g of ethanolamine, 140 g of ammonia, 10 g of water, 5.74 g of catalyst 6, and 11.8 Nl of hydrogen are placed in the autoclave of example 1. The mixture is agitated for 8 hrs. at a temperature of 195° C. and a pressure of 149 bars absolute. The results are shown in the tables below.

| % E.A. Converted | | Yield in weight %/Initial E.A. | | Wt. % Yield/E.A. Consumed | |
| --- | --- | --- | --- | --- | --- |
| into E.D.A. | 34.2 | of E.D.A. | 33.6 | of E.D.A. | 58.8 |
| into PIP | 13.0 | of PIP | 9.2 | of PIP | 16.0 |
| into heavy product | 10.0 | of heavy product | 7.8 | of heavy product | 13.6 |
| TOTAL | 57.2 | of H$_2$O | 36.8 | | |
| | | of unconverted E.A. | 42.8 | | |
| | | TOTAL | 130.2 | | |

EXAMPLE 7:

Catalyst 7: (Ni-Co on alumina). The following are dissolved in 1.8 l of water: 148.2 g of crystallized cobalt nitrate, 148.6 g of crystallized nickel nitrate, and 441 g of crystallized aluminum nitrate. A soda solution (2.4 l) containing 222 g of NaOH is added to this solution while stirring. The suspension obtained is filtered then rinsed with 4 l of water at 20° C. The precipitate is dried at 90° C. for 12 hrs. then decomposed in air for 5 h at 400° C., the temperature rising gradually at the rate of 50° C./hr. After forming into cylindrical pellets (5×5 mm) it is reduced in an N$_2$+3H$_2$ mixture (300 Nl/h) at 450° C. for 8 hrs. (temperature rise of 50° C./hr.). The nickel content of the catalyst is 25%, the cobalt content is 25%, and the sodium content 0.2%; the specific surface is 124 m$^2$/g.

Application: 50 g of ethanolamine, 140 g of ammonia, 7.8 g of catalyst 7, and 11.8 Nl of hydrogen are placed in the above autoclave. The mixture is stirred for 8 hrs. at 205° C. and a pressure of 204 bars absolute. The results are shown in the tables below.

| % E.A. Converted | | Yield in weight %/Initial E.A. | | Wt. % Yield/E.A. Consumed | |
| --- | --- | --- | --- | --- | --- |
| into E.D.A. | 37.2 | of E.D.A. | 36.6 | of E.D.A. | 54.8 |
| into PIP | 19.5 | of PIP | 13.8 | of PIP | 20.6 |
| into heavy product | 10.3 | of heavy product | 7.7 | of heavy product | 11.5 |
| TOTAL | 67.0 | of H$_2$O | 19.6 | | |
| | | of unconverted E.A. | 33.1 | | |
| | | TOTAL | 110.8 | | |

EXAMPLE 8

Catalyst 8: (Ni on thorium oxide). The following are dissolved in 3.5 l of demineralized water: 495 g of crystallized nickel nitrate, 313.7 g of crystallized thorium nitrate Th(NO$_3$)$_4$. 4H$_2$O. 1.7 l of soda solution containing 227 g of NaOH is added under agitation. The precipitate is filtered then rinsed with 6 l of water. It is then dried at 80° C. for 15 hrs. and decomposed in air at 400° C. for 5 hrs. (temperature rise 50° C./hr). After forming into pellets (5×5 mm) it is reduced at 450° C. in a mixture of N$_2$+3H$_2$ (500 Nl/h) for 8 hrs. (temperature rise 50° C./hr). The weight of the product obtained is 245 g. The nickel content of the catalyst is 40%. Its specific surface is 60 m$^2$/g.

Application: 50 g of ethanolamine, 140 g of ammonia, 10 g of water, 6.80 g of catalyst 8 and 11.8 Nl of hydrogen are placed in the autoclave. The mixture is stirred for 8 h at a temperature of 195° C. and a pressure of 150 bars absolute. The results are shown in the table below.

| % E.A. Converted | | Yield in weight %/Initial E.A. | | Wt. % Yield/E.A. Consumed | |
| --- | --- | --- | --- | --- | --- |
| into E.D.A. | 38.3 | of E.D.A. | 37.7 | of E.D.A. | 59.0 |
| into PIP | 20.6 | of PIP | 14.5 | of PIP | 22.7 |
| into heavy product | 5.0 | of heavy product | 4.0 | of heavy product | 6.2 |
| TOTAL | 63.9 | of H$_2$O | 38.8 | | |
| | | of unconverted E.A. | 36.1 | | |
| | | TOTAL | 131.1 | | |

EXAMPLE 9

Catalyst 9: (Nickel on cerium oxide). The following are dissolved in 2.6 l of water: 495.6 g of crystallized nickel nitrate, 378.5 g of crystallized cerium nitrate Ce(NO$_3$)$_3$.6H$_2$O. 2 l of soda solution containing 270 g of NaOH are added while stirring. The precipitate is raised to a temperature of 80° C. for 15 minutes then filtered after cooling to 40° C. and rinsed with 7.5 l of demineralized water. It is treated in air at 250° C. for 10 hrs. (temperature rise 50° C./h). The product is finely ground then reduced in a horizontal furnace while being scavenged with N$_2$+3H$_2$ at 400° C. for 10 hrs (temperature rise 50° C./h). The nickel content of the catalyst is 40% and the specific surface is 50 m$^2$/g.

Application: 50 g of ethanolamine, 140 g of ammonia, 10 g of water, 6.83 g of catalyst 9, and 11.8 Nl of hydrogen are placed in the autoclave. The mixture is agitated for 8 h at a temperature of 195° C. and a pressure of 161 bars absolute. The results are shown in the tables below.

| % E.A. Converted | | Yield in weight %/Initial E.A. | | Wt. % Yield/E.A. Consumed | |
| --- | --- | --- | --- | --- | --- |
| into E.D.A. | 32.4 | of E.D.A. | 31.9 | of E.D.A. | 67.8 |
| into PIP | 11.3 | of PIP | 8.0 | of PIP | 17.0 |
| into heavy product | 3.3 | of heavy product | 2.6 | of heavy product | 5.5 |
| TOTAL | 47.0 | of H$_2$O | 33.8 | | |
| | | of unconverted E.A. | 53.0 | | |
| | | TOTAL | 129.3 | | |

EXAMPLE 10

Catalyst 10: (Nickel on silica). 1.5 l of an ammonia solution (13.5 moles/l) are added to 420.8 g of a nickel nitrate solution, density 1.53, containing 14.26 wt. % nickel. The nickel is in the form of a soluble nickel tetramine complex. 222 g of a sodium silicate soution, 27 wt. % SiO$_2$, are added under vigorous agitation. The excess ammonia is evaporated slowly at 70°–80° C. while agitation continues. The precipitate obtained is filtered then rinsed with 4 l of demineralized water. After drying at 80° C. for 12 h it is ground, mixed with 1% graphite, formed into 5×5 mm cylindrical pellets, then reduced directly in an N$_2$+3H$_2$ mixture (300 Nl/h) at 450° C. for 8 h (temperature rise 50° C./h). The nickel content of the catalyst is 50% and its specific surface is 146 m$^2$/g.

Application: 50 g of ethanolamine, 140 g of ammonia, 7.8 g of catalyst 10, and 11.8 Nl of hydrogen are placed in the above autoclave. The mixture is agitated for 8 h at 205° C. and 189 bars absolute. The results are grouped in the tables below.

| % E.A. Converted | | Yield in weight %/Initial E.A. | | Wt. % Yield/E.A. Consumed | |
|---|---|---|---|---|---|
| into E.D.A. | 22.2 | of E.D.A. | 21.8 | of E.D.A. | 46.9 |
| into PIP | 15.4 | of PIP | 10.9 | of PIP | 23.3 |
| into heavy product | 9.0 | of heavy product | 6.5 | of heavy product | 13.9 |
| TOTAL | 46.6 | of H$_2$O | 13.6 | | |
| | | of unconverted E.A. | 53.4 | | |
| | | TOTAL | 106.2 | | |

EXAMPLE 11

Catalyst 11: (Nickel on silica-alumina). 143 g of sodium aluminate solution, density 1.52, containing 360 g/l of Al$_2$O$_3$, are mixed under vigorous agitation with 185 g of sodium silicate solution, 27 wt. % SiO$_2$. 495 g of crystallized nickel nitrate are dissolved in 1.4 l of water; 250 cc of ammonia (13.5 mole/l NH$_3$) are then added; the solution obtained is a light blue. The two solutions are mixed; because of the high density of the sodium silicate, vigorous agitation is required to achieve homogenization. The ammonia is then evaporated slowly at 70°-80° C. under agitation. The precipitate obtained is filtered and rinsed with 5.5 l of demineralized water. After drying at 80° C. for 15 h, it is decomposed at 400° C. in air for 5 h then formed into 5×5 mm cylindrical pellets; the temperature rise is 50° C./h. It is then reduced at 450° C. for 10 h in an N$_2$+3H$_2$ mixture (400 Nl/h), with temperature rising gradually from ambient temperature to 450° C. at the rate of 50° C./h. The nickel content of the catalyst is 54.4%, the Al$_2$O$_3$ content is 18.4%, the SiO$_2$ content is 27.2% and the specific surface is 239 m$^2$/g.

Application: 50 g of ethanolamine, 140 g of ammonia, 10 g of water, and 7.50 g of catalyst 11 and 11.8 Nl of hydrogen are placed in the autoclave. The mixture is agitated for 8 h at 195° C., 141 bars absolute. The results are shown in the tables below.

| % E.A. Converted | | Yield in weight %/Initial E.A. | | Wt. % Yield/E.A. Consumed | |
|---|---|---|---|---|---|
| into E.D.A. | 29.4 | of E.D.A. | 28.9 | of E.D.A. | 47.0 |
| into PIP | 18.5 | of PIP | 13.1 | of PIP | 21.3 |
| into heavy product | 13.6 | of heavy product | 10.1 | of heavy product | 16.4 |
| TOTAL | 61.5 | of H$_2$O | 38.0 | | |
| | | of unconverted E.A. | 38.5 | | |
| | | TOTAL | 128.6 | | |

EXAMPLE 12

Catalyst 12: (Nickel on alumina); 100 g of aluminum balls (specific surface 350 m$^2$/g, mean pore diameter 60 Å) screened through a 2-5 mm mesh and predried at 120° C. for 8 h are treated with 80 cc of soda (NaOH 150 g/l) for ½ h. After filtering out the nonimpregnated soda solution, they are dried again at 120° C. for 4 h then impregnated for 2 h with molten nickel nitrate obtained by melting 140 g of crystallized nickel nitrate at 80° C. The temperature remains at 80° C. throughout the impregnation to prevent the nickel nitrate from crystallizing. The balls are then dried at 80° C. for 5 h and treated in air at 400° C.; this treatment causes nitrous vapors to be given off. To prevent an excessively violent reaction the temperature is raised gradually from 125° C. at the rate of 25° C./h up to 250° C. and the temperature of 400° C. is maintained for 4 h.

They are then reduced in an N$_2$+3H$_2$ mixture (200 Nl/h) at 450° C. for 8 h (temperature rise 50° C./h). The nickel content of the catalyst is 16.7% and the sodium content is 2.2%.

Application: 50 g of ethanolamine, 140 g of ammonia, 10 g of water, 8.4 g of catalyst 12 and 11.8 Nl of hydrogen are placed in the autoclave. The mixture is stirred for eight hours at 195° C., 159 bars absolute with agitation. The results are shown in the tables below.

| % E.A. Converted | | Yield in weight %/Initial E.A. | | Wt. % Yield/E.A. Consumed | |
|---|---|---|---|---|---|
| into E.D.A. | 17.4 | of E.D.A. | 17.1 | of E.D.A. | 87.2 |
| into PIP | 0.6 | of PIP | 0.4 | of PIP | 2.2 |
| into heavy product | 1.6 | of heavy product | 1.2 | of heavy product | 6.2 |
| TOTAL | 19.6 | of H$_2$O | 25.8 | | |
| | | of unconverted E.A. | 80.4 | | |
| | | TOTAL | 124.9 | | |

EXAMPLE 13

Catalyst 13: (Nickel on alumina). The following are dissolved in 2.8 l of water: 495.4 g of crystallized nickel nitrate and 735.5 g of aluminum nitrate. 2.8 l of a soda solution containing 372 g NaOH are added with agitation. The precipitate obtained is filtered then rinsed with 6 l of water. It is then dried at 90° C. for 12 h and then treated at 300° C. in air for 5 h (temperature rise from ambient temperature to 300° C. at the rate of 50° C./h). The product obtained after cooling is ground to a fine powder, mixed with 1% graphite, then formed into 5×5 mm pellets; the pellets are reduced in an N$_2$+3H$_2$ mixture (400 Nl/h); the reducing gas introduced is cold; the temperature is raised at the rate of 50° C./h to 450° C. and held at this temperature for 8 h. The nickel content of the catalysts is 50%.

Five other catalysts with various nickel contents are prepared by the same method.

| Catalyst 14: | 10% Ni |
|---|---|
| Catalyst 15: | 30% Ni |
| Catalyst 16: | 44% Ni |
| Catalyst 17: | 70% Ni |
| Catalyst 18: | 85% Ni |

The specific surface of catalysts 13 to 18 is approximately 100 m$^2$/g.

Application: 50 g of ethanolamine, 140 g of ammonia, 10 g of water, 7.5 g of one of catalyst 13 to 18, and 11.8 Nl of hydrogen are placed in the autoclave. They are agitated for 8 h at 195° C., pressure 146 bars absolute. The results are shown in the table below.

| Transformation % of E.A. | Catalyst 14 | Catalyst 15 | Catalyst 16 | Catalyst 13 | Catalyst 17 | Catalyst 18 |
|---|---|---|---|---|---|---|
| into E.D.A. | 8.1 | 18.0 | 27.7 | 31.6 | 32.8 | 34.4 |
| into PIP | 0.4 | 1.8 | 8.1 | 10.3 | 13.4 | 21.6 |
| into heavy | | | | | | |

| Transformation % of E.A. | Catalyst 14 | Catalyst 15 | Catalyst 16 | Catalyst 13 | Catalyst 17 | Catalyst 18 |
|---|---|---|---|---|---|---|
| products | 0 | 1.6 | 5.5 | 6.2 | 8.8 | 12.8 |
| TOTAL | 8.5 | 21.4 | 41.3 | 48.1 | 55.0 | 68.8 |

EXAMPLE 14

150 cc of catalyst 4 in 5×5 mm pellets are placed in an open vertical reactor; the catalyst is reduced in situ; the flow-rate of reducing gas ($N_2+3H_2$) is 800 Nl/h; the temperature of 450° C. is maintained for 3 h. The reactor is supplied continuously from top to bottom with 72.2 g/h of ethanolamine, 500 g/h of ammonia, and 40 Nl/h of hydrogen, preheated to 215° C.; a pressure of 200 bars absolute is maintained and the catalytic bed temperature is 215° C. The hourly throughput (the ratio between the total gas flowrate in Nl/h and the catalyst volume in liters) is 4855 $h^{-1}$; the contact time between the ethanolamine and the catalyst is 83 seconds.

The results obtained after 4212 h of operation are shown in the tables below:

| % E.A. Converted | | Yield in weight %/Initial E.A. | | Wt. % Yield/E.A. Consumed | |
|---|---|---|---|---|---|
| into E.D.A. | 31.9 | of E.D.A. | 31.4 | of E.D.A. | 59.4 |
| into PIP | 11.7 | of PIP | 8.2 | of PIP | 15.6 |
| into heavy product | 9.3 | of heavy product | 6.8 | of heavy product | 12.9 |
| TOTAL | 52.9 | of H$_2$O | 15.3 | | |
| | | of unconverted E.A. | 47.2 | | |
| | | TOTAL | 108.9 | | |

EXAMPLE 15

150 cc of catalyst 5 in 5×5 mm pellets are placed in the open vertical reactor; the catalyst is reduced in situ; the flowrate of the reducing gas ($N_2+3H_2$) is 800 Nl/h; the temperature of 450° C. is maintained for 3 h. The reactor is supplied continuously from top to bottom with 72.6 g/h of ethanolamine, 481 g/h of ammonia, and 46.4 Nl/h of hydrogen, preheated to 220° C.; a pressure of 200 bars absolute is maintained and the temperature of the catalytic bed is 220° C. The hourly throughput is 4750 $h^{-1}$; the contact time between the ethanolamine and the catalyst is 84 seconds. The results obtained after 4508 h of operation are shown in the tables below:

| % E.A. Converted | | Yield in weight %/Initial E.A. | | Wt. % Yield/E.A. Consumed | |
|---|---|---|---|---|---|
| into E.D.A. | 36.8 | of E.D.A. | 36.2 | of E.D.A. | 67.1 |
| into PIP | 8.5 | of PIP | 6.0 | of PIP | 11.1 |
| into heavy product | 8.7 | of heavy product | 6.3 | of heavy product | 11.7 |
| TOTAL | 54.0 | of H$_2$O | 15.7 | | |
| | | of unconverted E.A. | 46.0 | | |
| | | TOTAL | 110.2 | | |

EXAMPLE 16

Two series of tests, with and without piperazine recycling, are conducted in the open vertical reactor charged with catalyst 4 of Example 14.

The test conditions and results obtained are shown in the tables below:

| Conditions | | Case 1 | Case 2 | Case 3 | Case 4 |
|---|---|---|---|---|---|
| Inlet flowrates | E.A. g/h | 72.0 | 67.7 | 71.7 | 66.5 |
| | PIP g/h | 0 | 4.3 | 0 | 5.2 |
| | NH$_3$ g/h | 505 | | 500 | |
| | H$_2$ Nl/h | 41.0 | | 43.8 | |
| Catalyst temp. °C. | | 210 | | 215 | |
| Pressure bars absolute | | 200 | | 170 | |
| Hourly throughput $h^{-1}$ | | 4900 | | 4850 | |
| Contact time: E. A. or mixture (EA, PIP) | | 82 | | 72 | |

| Results, Cases 1 and 2 | | |
|---|---|---|
| % E.A. Converted | Case 1 | Case 2 |
| into E.D.A. | 27.9 | 30.9 |
| into PIP | 10.1 | 4.5 |
| into heavy product | 9.3 | 9.7 |
| TOTAL | 47.3 | 45.1 |
| Yield in weight %/Initial E.A. | Case 1 | Case 2 |
| of E.D.A. | 27.4 | 30.4 |
| of PIP | 7.1 | 3.2 |
| of heavy product | 6.8 | 7.1 |
| of H$_2$O | 13.6 | 13.0 |
| of unconverted E.A. | 52.8 | 54.9 |
| TOTAL | 107.7 | 108.6 |
| Yield, Wt. %/E.A. Consumed | Case 1 | Case 2 |
| in E.D.A. | 58.0 | 67.4 |
| in PIP | 15.1 | 7.0 |
| in heavy products | 14.4 | 15.8 |

| Results, Cases 3 and 4 | | |
|---|---|---|
| % E.A. Converted | Case 3 | Case 4 |
| into E.D.A. | 23.9 | 25.8 |
| into PIP | 6.5 | 1.6 |
| into heavy product | 7.8 | 9.7 |
| TOTAL | 38.2 | 37.1 |
| Yield in weight %/Initial E.A. | Case 3 | Case 4 |
| of E.D.A. | 23.5 | 25.4 |
| of PIP | 4.6 | 1.1 |
| of heavy product | 5.7 | 7.0 |
| of H$_2$O | 11.0 | 10.6 |
| of unconverted E.A. | 61.9 | 63.0 |
| TOTAL | 106.7 | 107.1 |
| Yield, Wt. %/E.A. Consumed | Case 3 | Case 4 |
| in EDA | 61.7 | 68.5 |
| in PIP | 12.0 | 3.1 |
| in heavy products | 14.8 | 18.9 |

EXAMPLE 17

Catalyst 19: (nickel on alumina). The following are disolved in 1 l of water: 735 g of crystallized aluminum nitrate (Al(NO₃)₃.9H₂O) and 389 g of crystallized nickel nitrate (Ni(NO₃)₂.6H₂O). To this solution, 800 cc of a soda solution (sodium carbonate) containing 342 g of NaOH are added with agitation.

The suspension is then boiled for 20 minutes; after cooling to 30° C., the precipitate is filtered out on fritted glass, then washed with about 400 cc of water at 20° C.; the volume of water used is determined in order to keep the amount of sodium salts formed at the level indicated below. The product is then dried at 80° C., and subsequently decomposed at 350° C. for six hours. After mixing with 2% graphite, the powder is shaped into 5×5 mm cylindrical tablets.

The catalyst is reduced in situ by adding 130 cc of catalyst to a vertical open reactor and treating with reducing gas at 450° C. for 8 hours. The temperature increase is 50° C. per hour.

The Ni and Na contents of the reduced catalyst are 39.2% and 8% respectively. The specific surface is 43 m²/g. The mechanical crushing strength of the catalyst is about 50 kg on the flat surfaces.

Application: The reactor is continuously fed from top to bottom with 69.2 g/h of ethanolamine, 249 g/h of ammonia, 215 Nl/h of hydrogen preheated to 215° C.; a pressure of 185 bars absolute is maintained, and the temperature of the catalytic bed is 215° C. The hourly throughput is 5600 h⁻¹; the contact time between the ethanolamine and the catalyst is about 67 seconds.

The results obtained, after 5030 hours of operations, are summarized in the tables below and are practically identical to those at the beginning of the operation.

| % E.A. Converted | | Yield in weight %/Initial E.A. | | Wt. % Yield/E.A. Consumed | |
| --- | --- | --- | --- | --- | --- |
| into E.D.A. | 31.4 | of E.D.A. | 30.9 | of E.D.A. | 70.7 |
| into PIP | 6.6 | of PIP | 4.6 | of PIP | 10.6 |
| into heavy product | 5.7 | of heavy product | 4.4 | of heavy product | 10.1 |
| TOTAL | 43.7 | of H₂O | 12.9 | | |
| | | of unconverted E.A. | 56.3 | | |
| | | TOTAL | 109.1 | | |

Conclusion

Activity remained perfectly stable and an examination of the catalyst revealed that it had not undergone any changes, with the mechanical strength at 5030 hours being 55 kg on the flat surfaces.

EXAMPLE 18

Catalyst 20: (nickel, sodium, and rhodium on alumina). A solution of aluminum nitrate (1200 cc), containing 459.7 g of nitrate Al(NO₃)₃ . 9H₂O, is added to 286.5 cc of a solution of nickel nitrate with a density of 1.53 containing 14.26% Ni by weight. The resultant solution is added with agitation to a soda solution of 100 g, containing 232.5 g of NaOH. The suspension is boiled for 10 minutes; after cooling, it is filtered through a filter funnel and rinsed with 300 cc of water at 20° C. The threshold for stopping rinsing is determined in order to obtain a sodium salt content at a level as indicated below. The precipitate is dried at 100° C., then decomposed at 350° C., by raising the temperature gradually at the rate of 50° C. per hour and keeping the level at 350° C. for 6 hours. The product is ground finely, then impregnated with 55 cc of a solution of a rhodium salt (ammonium chlororhodate, (NH₄)₂ RhCl₅ . H₂O) containing 71.6 mg of rhodium. After drying at 80° C., the product is mixed with 2% graphite, then molded into cylindrical tablets measuring 5×5 mm.

The catalyst (130 cc) is loaded into a vertical open reactor and the catalyst is then reduced in situ, mixing with a reducing gas at 450° C. for 8 hours.

The Ni, Rh, and Na contents of the reduced catalyst are 43.6%, 0.05%, and 9.5%, respectively. The specific surface is 37 m²/g. The mechanical crushing strength of the catalyst is 62 kg on the flat surfaces.

Application

The reactor is continuously fed from top to bottom with 69.4 g/h of ethanolamine, 493 g/h of ammonia, and 70 Nl/h of hydrogen preheated to 215° C.; a pressure of 190 bars absolute is maintained and the temperature of the catalytic bed is kept at 215° C. The hourly throughput is 5800 h⁻¹, and the contact time of the ethanolamine with the catalyst is 66 seconds.

The results obtained after 4823 hours of operation are summarized in the tables below and are practically identical to those at the beginning of the operation.

| % E.A. Converted | | Yield in weight %/Initial E.A. | | Wt. % Yield/E.A. Consumed | |
| --- | --- | --- | --- | --- | --- |
| into E.D.A. | 32.2 | of E.D.A. | 31.7 | of E.D.A. | 69.2 |
| into PIP | 7.3 | of PIP | 5.1 | of PIP | 11.2 |
| into heavy product | 6.3 | of heavy product | 4.8 | of heavy product | 10.4 |
| TOTAL | 45.8 | of H₂O | 13.4 | | |
| | | of unconverted E.A. | 54.2 | | |
| | | TOTAL | 109.2 | | |

Conclusion

The activity is higher because of the presence of the rhodium. The activity remains perfectly stable. The catalyst does not undergo any change, and the mechanical strength is preserved; 70 kg is found.

It will be obvious to those skilled in the art that various changes may be made without departing from the scope of the invention and the invention is not to be considered limited to what is described in the specification.

What is claimed is:

1. Amination catalyst comprising at least one active metal from the group of transition metals consisting of nickel, cobalt and copper, uniformly combined with a refractory microporous substrate with a specific surface between 10 and 300 m²/g and a pore diameter less than 5,000 A, wherein the transition metal content represents 30–70% of the total catalyst weight.

2. Amination catalyst according to claim 1, wherein the active metal is nickel, alone or in combination with cobalt and/or copper, nickel representing at least 50% of the active substance.

3. Amination catalyst according to claim 1, wherein the microporous substrate comprises at least one refractory oxide selected from the group consisting of alumina, silica, thorium oxide and cerium oxide.

4. Amination catalyst according to claim 1, wherein the combination of transition metal and microporous substrate is in a structural edifice being obtained by coprecipitation of all the catalyst elements from soluble salts, directly reducible to the desired catalyst elements, the obtained precipitate being filtered, rinsed and then dried at a temperature between 80° and 120° C. or by impregnation with soluble salts of the active elements, directly reducible to the desired active elements, on precombined refractory oxides, the impregnated substrate being then dried at a temperature between 80° and 120° C., the coprecipitate or impregnated substrate then being subjected to heat treatment in air at a temperature between 350° and 500° C. for several hours with a gradual temperature rise of 50° C./h from ambient temperature, and then subjected to direct reduction by being scavenged with a reducing gas between 400° and 500° C. for several hours, with a temperature rise of 50° C./h from ambient temperature to the reduction temperature.

5. Amination catalyst according to claim 1, wherein the specific surface is between 30 and 50 m$^2$/g.

6. Amination catalyst according to claim 1, wherein the catalyst further contains a stabilizer comprising a sodium-based compound, added in an amount between 0.15 and 20% expressed in sodium relative to the weight of the catalyst.

7. Amination catalyst according to claim 6, wherein the sodium content is between 5 and 10% by weight.

8. Amination catalyst according to claim 1, wherein the catalyst further contains a promoter associated with said active metal, said promoter comprising a rhodium-based compound whose maximum content is 0.1% by weight of rhodium relative to the weight of the catalyst.

9. Amination catalyst according to claim 6, wherein the catalyst further contains a promoter associated with said active metal, said promoter comprising a rhodium-based compound whose maximum content is 0.1% by weight of rhodium relative to the weight of the catalyst.

10. A method of making the catalyst in accordance with claim 1 comprising:
  coprecipitating all of the catalyst elements from soluble salts directly reducible to the desired catalyst elements or impregnating soluble salts of the active elements, directly reducible to the desired active element, into precombined refractory oxides;
  heat treating in air at a temperature between 350° and 500° C. for several hours with a gradual temperature rise of 50° C./h from ambient temperature; and
  reducing the heat treated product by scavenging with a reducing gas at a temperature between 400° C. and 550° C. for several hours, with a temperature rise of 50° C. from ambient temperature to the reduction temperature.

* * * * *